US010849880B2

(12) United States Patent
Okada et al.

(10) Patent No.: US 10,849,880 B2
(45) Date of Patent: Dec. 1, 2020

(54) PHARMACEUTICAL COMPOSITION

(71) Applicant: FUJIFILM Toyama Chemical Co., Ltd., Tokyo (JP)

(72) Inventors: Kotaro Okada, Ashigarakami-gun (JP); Yoshinori Sakata, Ashigarakami-gun (JP); Shigetomo Tsujihata, Ashigarakami-gun (JP)

(73) Assignee: FUJIFILM Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 16/474,408

(22) PCT Filed: Dec. 28, 2017

(86) PCT No.: PCT/JP2017/047253
§ 371 (c)(1),
(2) Date: Jun. 27, 2019

(87) PCT Pub. No.: WO2018/124283
PCT Pub. Date: Jul. 5, 2018

(65) Prior Publication Data
US 2019/0336477 A1 Nov. 7, 2019

(30) Foreign Application Priority Data
Dec. 28, 2016 (JP) .................. 2016-255624

(51) Int. Cl.
| | | |
|---|---|---|
| A61K 31/397 | (2006.01) | |
| A61K 9/16 | (2006.01) | |
| A61K 9/20 | (2006.01) | |
| A61K 47/12 | (2006.01) | |
| A61K 47/18 | (2017.01) | |
| A61K 47/32 | (2006.01) | |

(52) U.S. Cl.
CPC .............. *A61K 31/397* (2013.01); *A61K 9/16* (2013.01); *A61K 9/2086* (2013.01); *A61K 47/12* (2013.01); *A61K 47/18* (2013.01); *A61K 47/32* (2013.01)

(58) Field of Classification Search
CPC .................................... A61K 31/397
USPC .................................... 514/210.19
See application file for complete search history.

(56) References Cited

U.S. PATENT DOCUMENTS

| | | | |
|---|---|---|---|
| 7,727,552 | B1 | 6/2010 | Ukai et al. |
| 2005/0070521 | A1 | 3/2005 | Saitoh et al. |
| 2010/0184997 | A1 | 7/2010 | Fukushima et al. |
| 2015/0045345 | A1 | 2/2015 | Inaba et al. |
| 2017/0165227 | A1 | 6/2017 | Takahashi et al. |

FOREIGN PATENT DOCUMENTS

| | | |
|---|---|---|
| EP | 2 048 145 A1 | 4/2009 |
| EP | 2 614 816 A1 | 7/2013 |
| EP | 2 719 377 A1 | 4/2014 |
| EP | 2 818 165 A1 | 12/2014 |
| EP | 3 100 725 A1 | 12/2016 |
| JP | 2009-051855 A | 3/2009 |
| JP | 2009-263298 A | 11/2009 |
| JP | 2012-107060 A | 6/2012 |
| JP | 2013-177418 A | 9/2013 |
| JP | 2016-141630 A | 8/2016 |
| WO | 03/035647 A | 5/2003 |
| WO | 2008/016107 A1 | 2/2008 |
| WO | 2009/022674 A1 | 2/2009 |
| WO | 2013/125617 A1 | 8/2013 |
| WO | 2015/115582 A1 | 8/2015 |
| WO | 2017/111005 A1 | 6/2017 |

OTHER PUBLICATIONS

Extended European Search Report (EESR) dated Nov. 27, 2019 from the European Patent Office in European application No. 17885808.0.
Written Opinion dated Feb. 27, 2018 from the International Bureau in counterpart International Application No. PCT/JP2017/047253.
International Search Report dated Feb. 27, 2018 from the International Searching Authority in counterpart International Application No. PCT/JP2017/047253.
International Preliminary Report on Patentability dated Jul. 2, 2019 from the International Bureau in counterpart International Application No. PCT/JP2017/047253.

*Primary Examiner* — Raymond J Henley, III
(74) *Attorney, Agent, or Firm* — Sughrue Mion, PLLC

(57) ABSTRACT

An object of the present invention is to provide a solid pharmaceutical composition which suppresses the characteristic bitter taste of 1-(3-(2-(1-benzothiophen-5-yl)ethoxy)propyl)azetidin-3-ol or a salt thereof and has a good storage stability of the-aforementioned compound or a salt thereof. The present invention provides a solid pharmaceutical composition comprising 1-(3-(2-(1-benzothiophen-5-yl)ethoxy)propyl)azetidin-3-ol or a salt thereof and a carboxylic acid whose solubility in water at 25° C. is 50 g/100 g $H_2O$ or less, wherein pH of a solution obtained when the solid pharmaceutical composition is dissolved or suspended in a 10 mmol/L KCl solution such that 1-(3-(2-(1-benzothiophen-5-yl)ethoxy)propyl)azetidin-3-ol or the salt thereof is 1 mg/mL or 8.96 mg/mL is 4.8 or less.

9 Claims, 1 Drawing Sheet

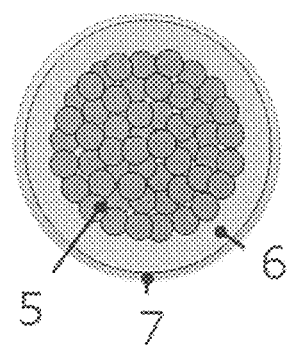

PHARMACEUTICAL COMPOSITION

CROSS REFERENCE TO RELATED APPLICATIONS

This application is a National Stage of International Application No. PCT/JP2017/047253 filed Dec. 28, 2017, claiming priority based on Japanese Patent Application No. 2016-255624 filed Dec. 28, 2016.

TECHNICAL FIELD

The present invention relates to a solid pharmaceutical composition comprising a predetermined drug and a predetermined carboxylic acid, wherein pH of a solution obtained when a predetermined amount is dissolved or suspended in a 10 mmol/L KCl solution is 4.8 or less.

BACKGROUND ART 1-(3-(2-(1-benzothiophen-5-yl)ethoxy)propyl)azetidin-3-ol (hereinafter also referred to as compound A) or a salt thereof has a neuroprotective action, a nerve regeneration promoting action, and a neurite outgrowth promoting action, and is a compound useful as a therapeutic agent for diseases of central and peripheral nerves (Patent Document 1).

Compound A or a salt thereof is orally administered, and as a pharmaceutical composition for oral administration, a solid pharmaceutical composition containing compound A or a salt thereof and one or two or more selected from mannitol, sorbitol, and isomaltose is known (Patent Document 2).

On the other hand, as a method of suppressing the bitter taste of a drug, blending of L-arginine (Patent Document 3), citric acid, tartaric acid (Patent Document 4), or lactic acid (Patent Document 5) is known. Furthermore, carrageenan and chondroitin sulfate are known as substances that suppress bitter taste (Patent Document 6).

PRIOR ART DOCUMENTS

Patent Documents

Patent Document 1: International Publication No. WO 2003/035647
Patent Document 2: International Publication No. WO 2013/125617
Patent Document 3: JP Patent Publication (Kokai) No. 2013-177418
Patent Document 4: JP Patent Publication (Kokai) No. 2009-263298
Patent Document 5: JP Patent Publication (Kokai) No. 2012-107060
Patent Document 6: JP Patent Publication (Kokai) No. 2009-51855

SUMMARY OF INVENTION

Object to be Solved by the Invention

Patients requiring compound A or a salt thereof are mainly elderly people, and an easier-to-take formulation is desired. Orally disintegrating tablets and granules are known as easy-to-take formulations, and a problem is that compound A has a characteristic bitterness, hi addition, another problem of compound A or a salt thereof is that it is easily decomposed during storage.

A problem of the techniques disclosed in Patent Documents 3 to 5 is that the bitter taste of compound A or a salt, thereof cannot be suppressed, or another problem is that its storage stability deteriorates. Moreover, when the technique of Patent Document 6 is applied to the maleate of compound A, the bitter taste which remains thereafter (post-bitter taste) cannot be suppressed.

An object of the present invention is to provide a solid pharmaceutical composition which suppresses the characteristic bitter taste of compound A or a salt thereof and has a good storage stability of compound A or a salt thereof.

Means for Solving the Object

The present inventors have intensively studied to solve the above problems, and found that a specific organic acid is blended with a solid pharmaceutical composition comprising compound A or a salt thereof, allowing manufacturing of a pharmaceutical composition with reduced bitter taste that remains thereafter (post-bitter taste), characteristic of compound A. Furthermore, the present inventors have found that the combination of compound A or a salt thereof and the specific organic acid described above reduces the decomposition of compound A or the sail thereof during storage. The present invention has been completed based on these findings.

Specifically, the present invention provides the following:
(1) A solid pharmaceutical composition comprising 1-(3-(2-(1-benzothiophen-5-yl)ethoxy)propyl)azetidin-3-ol or a salt thereof and a carboxylic acid whose solubility in water at 25° C. is 50 g/100 g $H_2O$ or less, wherein pH of a solution obtained when the solid pharmaceutical composition is dissolved or suspended in a 10 mmol/L KCl solution such that 1-(3-(2-(1-benzothiophen-5-yl)ethoxy)propyl)azetidin-3-ol or the salt thereof is 1 mg/mL or 8.96 mg/mL is 4.8 or less.
(2) The solid pharmaceutical composition according to (1), wherein the carboxylic acid is one or more selected from an acidic amino acid or an acidic polymer.
(3) The solid pharmaceutical composition according to (1) or (2), wherein the carboxylic acid is one or more selected from L-aspartic acid or L-glutamic acid.
(4) The solid pharmaceutical composition according to (1) or (2), wherein the carboxylic acid is a methacrylic acid copolymer.
(5) The solid pharmaceutical composition according to any one of (1) to (4), wherein the pH is 3.0 or more and 4.8 or less.
(6) The solid pharmaceutical composition according to any one of (1) to (5), wherein the solid pharmaceutical composition is a composition comprising fine granules comprising 1-(3-(2-(1-benzothiophen-5-yl)ethoxy)propyl)azetidin-3-ol or the salt thereof and the carboxylic acid whose solubility in water at 25° C. is 50 g/100 g $H_2O$ or less.
(7) The solid pharmaceutical composition according to (6), wherein the fine granules are fine granules having a core comprising at least 1-(3-(2-(1-benzothiophen-5-yl)ethoxy) propyl)azetidin-3-ol or the salt thereof and a binder, and a polymer layer with which a surface of tire core is coated.
(8) The solid pharmaceutical composition according to (6) or (7), wherein the content of the carboxylic acid in fine granules is 10 to 100% by mass based on the mass of 1-(3-(2-(1-benzothiophen-5-yl)ethoxy)propyl)azetidin-3-ol or the salt thereof.
(9) The solid pharmaceutical composition according to any one of (1) to (8), wherein the composition is a fine granule or a tablet.

(10) The solid pharmaceutical composition according to any one of (1) to (8), wherein the composition is an orally disintegrating tablet.

Advantageous Effects of Invention

The present invention provides a solid pharmaceutical composition which suppresses the characteristic bitter taste of compound A or a salt thereof and has a good storage stability of compound A or a salt thereof.

BRIEF DESCRIPTION OF DRAWING

FIG. 1 shows a schematic view of an example of the fine granules of the present invention.

EMBODIMENT OF CARRYING OUT THE INVENTION

In the present description, die numerical range shown using "to" means a range which includes the numerical value described before and after "to" as the minimum value and the maximum value, respectively.

In the present description, the amount of each component in the composition is, when a plurality of substances corresponding to the component are present in the composition, the total amount of the plurality of substances present in the composition, unless otherwise stated.

In the present description, "average particle size" means volume average particle size (Mv), which is a value measured using a laser diffraction scattering type particle size distribution measuring apparatus (product name: LS 13 320, Beckman Coulter. Inc.), and the method of measuring the average particle size is not particularly limited.

In the present description, the term "layer" includes not only the configuration of coating the entirety of the object to be coated and but also the configuration of coating a portion of the object to be coated.

[Solid Pharmaceutical Composition]

The solid pharmaceutical composition of the present invention is a solid pharmaceutical composition comprising compound A or a salt thereof and a carboxylic-acid whose solubility in water at 25° C. is 50 g/100 g $H_2O$ or less, wherein pH of a solution obtained when the solid pharmaceutical composition is dissolved or suspended in a 10 mmol/L KCl solution such that compound A or the salt thereof is 1 mg/mL or 8.96 mg/mL is 4.8 or less.

The present inventors have found that the bitter taste of compound A or a salt thereof consists of a bitter taste fell when contained in the oral cavity (pre-bitter taste) and a bitter taste that remains thereafter (post-bitter haste) The present invention has found the following unexpected effect: by blending compound A or a salt thereof and a carboxylic acid whose solubility in water at 25° C. is 50 g/100 g $H_2O$ or less such that the pH of a solution obtained when they are dissolved or suspended in a 10 mmol/L KCl solution such that compound A or the salt thereof is 1 mg/mL or 8.96 mg/ml, is 4.8 or less, to provide a solid pharmaceutical composition, allowing selective suppression of the post-bitter taste. Moreover, another unexpected effect has also been found: the specific carboxylic acid described above maintains die stability during storage of compound A or a sail thereof.

<Compound A>

In the present invention, compound A (that is, 1-(3-(2-(1-benzothiophen-5-yl)ethoxy)propyl)azetidin-3-ol)) or a salt thereof is used as an active ingredient.

Since a salt of compound A has a cyclic amino group, examples of the salt thereof include salts at commonly known basic groups.

Examples of salts at basic groups include salts with mineral acids such as hydrochloric acid, hydrobromic acid, nitric acid, and sulfuric acid; salts with organic-carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylene sulfonic acid, and naphthalene sulfonic acid.

Among the above salts, preferable salts are pharmacologically acceptable salts and more preferable salts are salts with maleic acid.

In the case of having isomers (for example, optical isomers, geometric isomers, and tautomers), compound A or a salt thereof may be any of ail these isomers and may be any of hydrates, solvates, and all crystal forms.

Compound A or a salt thereof can be manufactured by methods known per se or an appropriate combination thereof, or a method disclosed in Patent Document 1.

The content of compound A or a salt thereof in the solid pharmaceutical composition is 30 to 90% by mass, preferably 40 to 90% by mass, and more preferably 50 to 90% by mass.

<Carboxylic Acid>

The type of a carboxylic acid used in the present invention is not particularly limited as long as the solubility in water at 25° C. is 50 g/100 g $H_2O$ or less. Examples of a carboxylic acid usable include maleic acid. L-glutamic add hydrochloride, fumaric acid, ascorbic acid, L-aspartic acid, succinic acid, adipic acid, sorbic acid, L-glutamic acid, carboxy vinyl polymer, hypromellose phthalate, cellulose acetate phthalate, methacrylic acid copolymer, carboxymethyl ethyl cellulose, methacrylic acid copolymer, and L-arginine hydrochloride, and are not particularly limited.

Carboxylic acids are preferably one or more selected from acidic amino acids (L-aspartic acid, L-glutamic acid, and the like) or acidic polymer (carboxy vinyl polymer, methacrylic acid copolymer, carboxymethyl ethyl cellulose, methacrylic acid copolymer, and the like). Among them, L-aspartic acid, L-glutamic acid, or methacrylic acid copolymer is more preferable.

The amount of a carboxylic acid used is set so as to satisfy the condition: "pH of a solution obtained when the solid pharmaceutical composition is dissolved or suspended in a 10 mmol/L KCl solution such that compound A or the salt thereof is 1 mg/mL or 8.96 mg/mL is 4.8 or less".

<pH>

In the present invention, the pH of a solution obtained when the solid pharmaceutical composition is dissolved or suspended in a 10 mmol/L KCl solution such that compound A or the salt thereof is 1 mg/mL or 8.96 mg/mL is 4.8 or less. Satisfying this condition can suppress the characteristic bitter taste of compound A or a salt thereof and can improve the storage stability of compound A or a salt thereof. In addition, the above described pH can be adjusted with the type and the amount of a carboxylic acid to be used.

The above pH is preferably 3.0 or more and 4.8 or less, more preferably 3.5 or more and 4.5 or less, and still more preferably 3.8 or more and 4.2 or less.

<Fine Granule>

The solid pharmaceutical composition of the present invention is preferably a composition comprising fine granules comprising compound A or a salt thereof and a carboxylic acid whose solubility in water at 25° C. is 50 g/100 g H₂O or less.

The fine granules are preferably fine granules having cores comprising compound A or a salt thereof, a carboxylic acid and a binder, and polymer layers with which the surface of the above cores is coated.

The schematic diagram of an example of the above fine granules is shown in FIG. 1. In the fine granules shown in FIG. 1, the surface of a core 5 including the drug substance which is compound A is coated with a polymer layer 6, and the surface of the polymer layer 6 is further coated with an overcoat layer 7. The polymer layer 6 is a layer that functions as a bitter taste masking layer. The fine granules shown in FIG. 1 can increase the content of the drug substance, included in one granule.

The core preferably contains at least compound A or a salt thereof and the binder. The core preferably consists of core particles containing compound A or a salt thereof and the binder, and preferably does not contain core particles that do not contain compound A or a salt thereof. The method of preparing the core is not particularly limited, and a wet agitation method or the like is preferable. The method of preparing the core will be described below.

The surface of the core is coated with a polymer layer. The method of coating with a polymer layer is not specifically limited, and a method of spray-coating a core with the coating solution including the polymer is preferable. The method of forming the polymer layer will be described below.

The roundness of the fine granules is 0.8 or more, preferably 0.82 or more, more preferably 0.83 or more, further more preferably 0.84 or more, still more preferably 0.86 or more, and particularly preferably 0.87 or more. The upper limit of the roundness of fine granules is not particularly limited, and is at most 1.0.

The roundness is determined by microscopic observation of 5 to 15 particles and calculation of 4π×(area)/(square of perimeter) for the core using software (ImageJ, National Institutes of Health), and is expressed by the average value. In the case of a perfect circle, die roundness is 1.0.

<Binder>

The type of the binder used to form the core is not particularly limited as long as it is a substance that can be mixed with compound A or a salt thereof to form the core. Examples of the binder include hydroxypropyl cellulose, hydroxypropyl methy) cellulose, methyl cellulose, carmellose sodium, gum arabic, pregelatinized starch, polyvinyl alcohol (PVA), and polyvinyl alcohol/polyethylene glycol graft polymer. The binders may be used singly or in combinations of two or more. Among them, the binder is preferably hydroxypropyl cellulose, gum arabic, pregelatinized starch, or PVA, and particularly preferably hydroxypropyl cellulose.

The amount of a binder used is not particularly limited, and is preferably 2 to 30% by mass, more preferably 3 to 30% by mass, further more preferably 3 to 20% by mass, still more preferably 5 to 20% by mass, and particularly preferably 5 to 15% by mass, based on tire mass of compound A or the salt thereof.

<Additive in Core>

The core may consist of compound A or a salt thereof and the binder, or may be added with additives such as excipients, in addition to compound A or a salt thereof and the binder. Examples of additives can include sugars selected from crystalline cellulose, lactose monohydrate, sucrose, and glucose; sugar alcohol selected from mannitol, sorbitol, erythritol, maltitol, trehalose, xylitol, and isomalt; cellulose derivatives such as ethylcellulose, carmellose, carmellose calcium, croscarmellose sodium, and low substituted hydroxypropyl cellulose; starch derivatives such as sodium carboxymethyl starch and pregelatinized starch; polypyrrolidone derivatives such as crospovidone; cyclodextrins such as α-cyclodextrin, β-cyclodextrin, γ-cyclodextrin, hydroxypropyl β-cyclodextrin, and sulfobutylether β-cyclodextrin sodium; starches such as corn starch, potato starch, and partially pregelatinized starch; phosphates such as calcium hydrogen phosphate and anhydrous calcium hydrogen phosphate; and carbonates such as precipitated calcium carbonate, and lactose monohydrate is particularly preferable.

The content of additives such as excipients in the core is not particularly limited, and is generally 10 to 100% by mass based on the mass of compound A or tire salt thereof.

<Polymer Layer>

The surface of the core van be coated with a polymer layer. The type of a polymer constituting the polymer layer is not particularly limited as long as it can be used in the pharmaceutical composition, that is, pharmaceutically acceptable, and for example, ammonio alkyl methacrylate copolymer (such as product name: Eudragit® RS 100, which is a pH independent sustained release coating), methacrylic avid copolymer, ethyl cellulose, and ethyl acrylate/methyl methacrylate copolymer can be used. As the polymer, one may be used alone, or two or more polymers may be used in combination The amount of the polymer used is not particularly limited, and is preferably 5 to 100% by mass, more preferably 10 to 90% by mass, still more preferably 20 to 80% by mass based on the mass of compound A or the salt thereof.

The polymer layer may consist of the above described polymer or may comprise additives other than the above described polymer.

Examples of additives in the polymer layer include a carboxylic avid having the above described predetermined solubility, plasticizer (for example, triacetin and triethyl citrate), and surfactant (glyceryl monostearate, polysorbate 80 and the like), and are not particularly limited.

The amount of the above additive used is not particularly limited, and the content of each additive is generally 2 to 30% by mass based on the mass of the polymer.

<Overcoat Layer>

The fine granules may further have an overcoat layer with which the surface of the polymer layer is coated. The fine granules having the overcoat layer can further suppress adhesion or aggregation among fine granules.

The type of a component constituting the overcoat layer is not particularly limited as long as it can be used in die pharmaceutical composition, that is, pharmaceutically acceptable, and for example, excipients such as mannitol, anhydrous silicic acid (light anhydrous silicic acid and the like) can be used.

The content of the overcoat layer is generally 0.5% by mass to 20% by mass based on the total mass of the core, the polymer layer, and the overcoat layer.

<Content of Carboxylic Acid in Fine Granules>

When the solid pharmaceutical composition of the present invention comprises fine granules, the content of the carboxylic acid in the fine granules is preferably 1 to 100% by mass, more preferably 1 to 50% by mass, still more preferably 1 to 10% by mass, and particularly preferably 1 to 5% by mass, based on the mass of compound A or the salt thereof.

<Average Particle Size of Fine Granules>

The average particle size of fine granules in the present invention is, for example, preferably 100 μm to 1000 μm, more preferably 100 μm to 750 μm, and still more preferably 100 μm to 500 μm. By setting the average particle size of the fine granules within the above range, the roughness in the oral cavity can be further reduced when the pharmaceutical composition is disintegrated in the oral cavity, and thus an unpleasant feeling of taking can be avoided.

[Method of Manufacturing Solid Pharmaceutical Composition]

When the solid pharmaceutical composition of the present invention is a composition comprising fine granules comprising compound A or a salt thereof and a carboxylic acid whose solubility in water at 25° C. 50 g/100 g $H_2O$ or less, the solid pharmaceutical composition of the present invention can be manufactured by a general granulation method (for example, a wet agitation granulation method) using compound A or a salt thereof and the above predetermined carboxylic acid.

When the above fine granules are fine granules having a core comprising at least compound A or a salt thereof and a binder, and a polymer layer with which the surface of the above core is coated, the solid pharmaceutical composition of the present invention can be manufactured by the manufacturing method comprising: a step of manufacturing the core comprising, compound A or a salt thereof and the binder by the wet agitation granulation method using compound A or a salt thereof and the binder; and a step of forming the polymer layer on the surface of the above core.

<Manufacturing of Core Comprising Compound A or Salt Thereof and Binder>

The core can be manufactured by the wet agitation granulation method using compound A or a salt thereof, the binder, and the carboxylic acid if desired. The wet agitation granulation method is a method of manufacturing aggregated particles of powder by agitating while adding a suitable liquid binder to a fine powder.

The wet agitation granulation method can be performed using an agitated granulator. An example of an agitated granulator can include vertical granulator model FM-VG-01, manufactured by Powrex Corporation. and is not particularly limited.

The aqueous solution of the binder can be sprayed while agitating compound A or a salt thereof, the binder, and the carboxylic acid if desired in the agitated granulator. Then, the agitation is further performed, and a granulated material can be obtained.

The agitation speed at spraying the aqueous solution of the binder is not particularly limited, and the blade rotational speed can be preferably 200 rpm to 400 rpm and more preferably 250 rpm to 300 rpm, and the cross screw rotational speed can be preferably 1000 rpm to 4000 rpm and more preferably 2000 rpm to 0.3000 rpm.

The agitation speed of the agitation after spraying the aqueous solution of the binder is not particularly limited, and the blade rotational speed can be preferably 600 rpm to 1000 rpm and more preferably 700 rpm to 900 rpm, and the cross screw rotational speed can be preferably 1000 rpm to 4000 rpm and more preferably 2000 rpm to 3000 rpm.

Drying the granulated material obtained above allows manufacturing of a core comprising compound A or a salt thereof, a binder, and if desired a carboxylic acid. Drying can be performed using a fluidized bed granulator (for example, model FD-MP-01, manufactured by Powrex Corporation)

<Step of Forming Polymer Layer on Surface of Core>

The step of forming the polymer layer on the surface of the core can be performed by a general coating method. For example, a coating solution for a polymer layer may be prepared by dissolving the components constituting the polymer layer in a solvent and sprayed onto the core. The polymer layer may or may not comprise the carboxylic acid having the predetermined solubility described above. The carboxylic acid is preferably comprised in the core and at least one of the polymer layer and the outermost layer. The spray speed, spray time, solution temperature, drying conditions, and the like of the coating solution for a polymer layer are not particularly limited, and may be appropriately set according to the composition of the coating solution for a polymer layer, viscosity, particle size, and the like.

<Step of Forming Overcoat Layer on Surface of Polymer Layer>

Forming the overcoat layer on the surface of the polymer layer can manufacture fine granules having the overcoat layer with which the surface of the polymer layer is coated. However, the overcoat layer may or may not be provided.

The step of forming the overcoat layer can be performed by a general coating method and a powder addition method. For example, a coating solution for an overcoat layer may be prepared by dissolving the components constituting the overcoat layer in a solvent and sprayed onto the surface of the polymer layer. The spray speed, spray time, solution temperature, drying conditions, and the like of the coating solution for an overcoat layer are not particularly limited, and may be appropriately set according to the composition of the coating solution for an overcoat layer, viscosity particle size, and the like. In the powder addition method, the components constituting the overcoat layer may be added in the form of a powder and mixed.

[Form of Solid Pharmaceutical Composition]

The form of the solid pharmaceutical composition of the present invention is not particularly limited, and is preferably a solid formulation for oral use such as fine granules, tablets, and granules, and more preferably fine granules or tablets. The tablet is preferably an orally disintegrating tablet.

The tablet can be conventional coated tablets, for example, sugar-coated tablets, gelatin-encapsulated tablets, gastric-coated tablets, enteric-coated tablets, and water-soluble film-coated tablets, as required.

The tablet may be preferably an orally disintegrating tablet.

The orally disintegrating tablet may further comprise an excipient component outside the fine granules. The excipient component as used herein is a component that can contribute to improvement in the formability and the ease of taking of the tablet comprising fine granules. The excipient component may comprise pharmacologically acceptable pharmaceutical additives such as bitter taste inhibitors, odor adsorbents, excipients, disintegrants, lubricants, binders, fluidizers, sweeteners, flavors, and coloring agents, in the range which does not inhibit the effect of the present invention. The pharmaceutical additive may be one in which one component performs two or more functions. Specific examples of the excipient component can include those described in paragraph Nos. 0085 to 0095 of JP Patent Publication (Kokai) No. 2016-141630.

As the pharmaceutical additive, one may be used alone, or two or more may be used in combination.

The content of pharmaceutical additives in the excipient component comprised outside of fine granules can be set appropriately in consideration of the content ratio of fine granules in die orally disintegrating tablet, the average particle size of the fine granules, and the like.

[Properties of Solid Pharmaceutical Composition]

When the solid pharmaceutical composition of the present invention is a tablet, 40 to 1000 mg of compound A or a salt thereof per tablet is preferably comprised.

The shape of the solid pharmaceutical composition of the present invention is not particularly limited as long as it is pharmaceutically acceptable.

When the solid pharmaceutical composition of the present invention is a tablet, the shape of the tablet may be, for example, a round tablet or a modified tablet, and can be appropriately set in consideration of drug compliance.

When the solid pharmaceutical composition of the present invention is a tablet, the size of the tablet is not particularly limited as long as it is pharmaceutically acceptable. From the view point that tablets are often used for patients who have difficulty swallowing, the size of the tablet of the present invention is preferably as small as possible in consideration of its medicinal effects.

In the solid pharmaceutical composition of the present invention, from the viewpoint of drug efficacy, dissolution rate after 60 minutes in the Japanese Pharmacopoeia dissolution test (paddle method: paddle rotation speed of 50 rpm, dissolution test solution: 0.1 mol/L hydrochloric acid) assuming dissolution of drug in the stomach is preferably 40% or more, more preferably 45% or more, further more preferably 50% or more, still more preferably 60% or more, yet still more preferably 70% or more, and particularly preferably 80% or more.

[Method of Manufacturing Tablets]

When the solid pharmaceutical composition of the present invention is a tablet, the method of manufacturing the tablet is not particularly limited, and known methods can be used. The tablet of the present invention can be obtained, for example, by mixing fine granules and, if desired, an excipient component, tableting the obtained mixed powder, and drying it.

The method of mixing the fine granules and the excipient component is not particularly limited. Examples of the method of mixing the fine granules and the excipient component include a method of mixing using a known mixer such as a V-type mixer (Tsutsui Scientific Instruments Co., Ltd.) and a fluidized bed granulator (Powrex Corporation).

The conditions such as the time required for mixing van be appropriately adjusted depending on the types of fine granules and the excipient component.

The method of tableting the mixed powder of fine granules and an excipient component is not particularly limited. The temperature at tableting is not particularly limited, and can be appropriately set.

An example of die method of tableting the mixed powder of fine granules and an excipient component includes a method of tableting using a tableting machine such as a rotary tableting machine (product name: HT-AP-SS, Hata Tekkosho Co., Ltd.) or a high speed rotary type tableting machine (product name: AQUARIUS G. Kikusui Seisakusho Ltd.).

Method of drying tableted material obtained by tableting tire mixed powder is not particularly limited. Examples of the method of drying tableted material obtained by tableting the mixed powder include a method of drying by vacuum drying, fluidized bed drying, or the like.

[Administration of Solid Pharmaceutical Composition]

The administration method, dosage, and frequency of administration of the solid pharmaceutical composition of the present invention can be appropriately selected according to the age, body weight, and symptoms of the patient. The dose that can exert its medicinal effects may be typically administrated in a single dose or in several divided doses a day, and the dose of compound A or a salt thereof, for example, 40 to 1000 mg may typically be administrated to an adult in a single dose or in several divided doses a day.

Hereinafter, the present invention will be described in detail by the following Examples, but the present invention is not limited to these Examples.

EXAMPLES

Examples 1 to 19 and Comparative Examples 1 to 14

The pH was measured when the maleate of compound A and the additive were dissolved or suspended in a 10 mmol/L KCl solution in such a way as to reach the respective numerical values shown in Table 2 to Table 6.

For the additives shown in Table 2 to Table 6, the solubility in water at 25° C. was measured. The unit of the numerical values in the column of solubility in Table 2 to Table 6 is g/100 g $H_2O$.

The following evaluation was performed about the solid pharmaceutical composition obtained by mixing the maleate of compound A and the additive according to the composition shown in Table 2 to Table 6.

The results of the above measurement and evaluation are shown in Table 2 to Table 6.

<Evaluation of Bitter Taste (Post-Bitter Taste)>

The bitter taste of compound A or a salt thereof has nut only a bitter taste felt when contained in the oral cavity (pre-bitter taste) and but also a bitter taste which persits after swallowing (post-bitter taste). That is, compound A or a salt thereof is a compound having both the pre-bitter taste and the post-bitter taste.

Evaluation was performed using a taste sensing system (Intelligent Sensor Technology. Inc.: SA402B). This taste sensing system is a device capable of taking out a change in the membrane potential of the artificial lipid membrane as a signal, and a CPA value corresponding to the aftertaste can be obtained. The CTA value is defined as follows:

CPA value: Vr'−Vr. Change of membrane Potential caused by Adsorption.

Vr (mV): Measured value of reference solution before measuring control solution or sample solution Vr' (mV): Measured value of the reference solution measured again after measuring the control solution or sample solution The measurement was performed three times, and the average value was calculated for each CPA value of the control solution and each sample solution.

In the taste sensing system, after stabilization with reference solutions (30 mmol/L KCl and 0.3 mmol/L tartaric acid), CPA values in the control solution and each sample solution were measured. As the sensor used for measurement, AGO specific to basic bitter taste was used.

Separately, a sensory test was performed, and a calibration curve was created from the correlation between the bitter taste score of the sensory and the CPA value. The bitter taste score was calculated by interpolating the CPA value from the calibration curve.

Bitter Taste Score of Sensory:

1 Bitter taste that can be perceived at last
2 Understandable bitter taste
3 Bitter taste that can be perceived easily
4 Strong bitter taste 5 Unbearable bitter taste The test method is as follows.

The solid pharmaceutical composition was added to a 10 mmol/L KCl solution such that the concentration of the maleate of compound A was 1 mg/mL, and the mixture was agitated for 30 minutes with a stirrer to give a sample solution. In addition, a 10 mmol/L KCl solution was used as a control solution.

The evaluation criteria for bitter taste (post-bitter taste) are as follows:
A: 1.5 or less
B: Greater than 1.5 and 2.5 or less
C: Greater than 2.5

<Evaluation of Degradation Material>

The prepared solid pharmaceutical composition was subjected to a stress test that it was stored in a thermostat at 70° C. for 7 days. The storage stability was evaluated in terms of the amount of compound A decomposed by the following method.

The above stored solid pharmaceutical composition was adjusted with water/acetonitrile/pH 3.0 phosphate buffer (450:50:1) such that the maleate of compound A had 333 µg/mL and was filtered through a membrane filter to obtain a filtrate. The degradation material of compound A was quantified by high performance liquid chromatography (HPLC). The amount of the degradation material detected at a relative retention time of 0.94 with respect to compound A was quantified as the degradation material of compound A under the following measurement conditions. The amount of the degradation material (percentage relative to the amount of compound A) is shown in Table 2 to Table 6.

(HPLC Measurement Condition)
Detector: UV detector (detection wavelength: 230 nm)
Column: Waters Sunfire 3.0 mm×150 mm (3.5 µm)
Column temperature: 40° C.
Developing solvent:
A; Water/acetonitrile/pH 3.0 phosphate buffer=38:7:5
B; Water/acetonitrile pH 3.0 phosphate buffer=11:7:2
Flow rate: 0.45 mL/min
Sample cooler temperature: 5° C.
Injection volume: 10 µL

TABLE 1

| Time (minute) | Concentration of developing solvent A (% by mass) | Concentration of developing solvent B (% by mass) |
|---|---|---|
| 0 | 100 | 0 |
| 3 | 100 | 0 |
| 23 | 0 | 100 |
| 35 | 0 | 100 |
| 40 | 100 | 0 |
| 50 | 100 | 0 |

Evaluation criteria for the degradation material are as follows:
A: Less than 0.25%
B: 0.25% or more and less than 0.75%
C: 0.75% or more <Comprehensive Evaluation>

The evaluation criteria for the comprehensive evaluation are as follows:
A: A case that the evaluation of bitter taste is A and the evaluation of degradation material is A
B: A case that the evaluation of bitter taste is A and the evaluation of degradation material is B, a case that the evaluation of bitter taste is B and the evaluation of degradation material is A, or a case that the evaluation of bitter taste is B and the evaluation of degradation material is B
C: A case that at least one of the evaluation of bitter taste and the evaluation of degradation material is C

TABLE 2

The unit of a numerical value of each component in the table is mg/mL or parts by mass

|  |  | Example 1 | Example 2 | Example 3 | Example 4 | Example 5 | Example 6 | Example 7 |
|---|---|---|---|---|---|---|---|---|
| Drug substance | Maleate of compound A | 1 | 1 | 1 | 1 | 1 | 1 | 1 |
| Additive | Maleic acid | 1 |  |  |  |  |  |  |
|  | L-glutamic acid hydrochloride |  | 1 |  |  |  |  |  |
|  | Fumaric acid |  |  | 1 |  |  |  |  |
|  | Ascorbic acid |  |  |  | 1 |  |  |  |
|  | L-aspartic acid |  |  |  |  | 1 | 0.5 | 0.25 |
|  | pH | 2.2 | 2.5 | 2.6 | 3.2 | 3.2 | 3.3 | 3.4 |
|  | Solubility | 47.8 | 49.0 | 0.5 | 30.0 | 0.4 | 0.4 | 0.4 |
|  | Bitter taste (post-bitter taste) | 0.0 | 0.0 | 0.5 | 1.3 | 0.5 | 0.7 | 1.0 |
|  | Degradation material (70° C., 7 days) | 0.72% | 0.10% | 0.00% | 0.00% | 0.00% | 0.00% | 0.00% |
|  | Evaluation of bitter taste | A | A | A | A | A | A | A |
|  | Evaluation of degradation material | B | A | A | A | A | A | A |
|  | Comprehensive evaluation | B | A | A | A | A | A | A |

TABLE 3

The unit of a numerical value of each component in the table is mg/mL or parts by mass

|  |  | Example 8 | Example 9 | Example 10 | Example 11 | Example 12 | Example 13 | Example 14 |
|---|---|---|---|---|---|---|---|---|
| Drug substance | Maleate of compound A | 1 | 1 | 1 | 1 | 1 | 1 | 1 |
| Additive | L-aspartic acid | 0.1 |  |  |  |  |  |  |
|  | Succinic acid |  | 1 |  |  |  |  |  |
|  | Adipic acid |  |  | 1 |  |  |  |  |

TABLE 3-continued

The unit of a numerical value of each component in the table is mg/mL or parts by mass

|  |  | Example 8 | Example 9 | Example 10 | Example 11 | Example 12 | Example 13 | Example 14 |
|---|---|---|---|---|---|---|---|---|
|  | Sorbic acid |  |  |  | 1 |  |  |  |
|  | L-glutamic acid |  |  |  |  | 1 |  |  |
|  | Carboxyvinyl polymer |  |  |  |  |  | 1 |  |
|  | Hypromellose phthalate ester |  |  |  |  |  |  | 1 |
|  | pH | 3.6 | 3.1 | 3.3 | 3.3 | 3.4 | 3.5 | 3.7 |
|  | Solubility | 0.4% | 8.0% | 2.2% | 0.3% | 0.8% | 0.7% | 0.0% |
| Bitter taste | Post-bitter taste | 1.4 | 1.4 | 1.9 | 2.6 | 1.5 | 1.2 | 1.9 |
| Degradation material | 70° C., 7 days | 0.00% | 0.02% | 0.00% | 0.03% | 0.00% | 0.02% | 0.00% |
|  | Evaluation of bitter taste | A | A | B | B | A | A | B |
|  | Evaluation of degradation material | A | A | A | A | A | A | A |
|  | Comprehensive evaluation | A | A | B | B | A | A | B |

TABLE 4

The unit of a numerical value of each component in the table is mg/mL or parts by mass

|  |  | Example 15 | Example 16 | Example 17 | Example 18 | Example 19 |
|---|---|---|---|---|---|---|
| Drug substance | Maleate of compound A | 1 | 1 | 1 | 1 | 1 |
| Additive | Cellulose acetate phthalate | 1 |  |  |  |  |
|  | Methacrylic acid copolymer L |  | 1 |  |  |  |
|  | Carboxymethylethyl cellulose |  |  | 1 |  |  |
|  | Methacrylic acid copolymer LD |  |  |  | 1 |  |
|  | L-arginine hydrochloride |  |  |  |  | 1 |
|  | pH | 3.7 | 3.8 | 3.9 | 4.0 | 4.7 |
|  | Solubility | 0.0% | 0.0% | 0.0% | 0.0% | 10.0% |
|  | Bitter taste (post-bitter taste) | 1.8 | 0.0 | 2.5 | 1.4 | 1.3 |
|  | Degradation material (70° C., 7 days) | 0.00% | 0.00% | 0.00% | 0.00% | 0.00% |
|  | Evaluation of bitter taste | B | A | B | A | A |
|  | Evaluation of degradation material | A | A | A | A | A |
|  | Comprehensive evaluation | B | A | B | A | A |

TABLE 5

The unit of a numerical value of each component in the table is mg/mL or parts by mass

|  |  | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|
| Drug substance | Maleate of compound A | 1 | 1 | 1 | 1 | 1 | 1 | 1 |
| Additive | Carmellose calcium | 1 |  |  |  |  |  |  |
|  | Xanthan gum |  | 1 |  |  |  |  |  |
|  | Copper Carrageenan |  |  | 1 |  |  |  |  |
|  | Chondroitin sulfate |  |  |  | 1 |  |  |  |
|  | Calcium lactate |  |  |  |  | 1 |  |  |
|  | Aminoalkyl methacrylate copolymer E |  |  |  |  |  | 1 |  |
|  | L-histidnie |  |  |  |  |  |  | 1 |
|  | pH | 4.9 | 4.9 | 5.0 | 5.2 | 5.1 | 6.3 | 6.6 |
|  | Solubility | 0.0% | 0.1% | 0.5% | 1.0% | 4.0% | 0.0% | 4.2% |
|  | Bitter taste (post-bitter taste) | 3.1 | 3.2 | 2.9 | 3.8 | 3.6 | 4.3 | 3.1 |
|  | Degradation material (70° C., 7 days) | 0.01% | 0.01% | 0.01% | 0.01% | 0.02% | 0.07% | 0.01% |

TABLE 5-continued

The unit of a numerical value of each component in the table is mg/mL or parts by mass

|  | Comparative Example 1 | Comparative Example 2 | Comparative Example 3 | Comparative Example 4 | Comparative Example 5 | Comparative Example 6 | Comparative Example 7 |
|---|---|---|---|---|---|---|---|
| Evaluation of bitter taste | C | C | C | C | C | C | C |
| Evaluation of degradation material | A | A | A | A | A | A | A |
| Comprehensive evaluation | C | C | C | C | C | C | C |

TABLE 6

The unit of a numerical value of each component in the table is mg/mL or parts by mass

|  |  | Comparative Example 8 | Comparative Example 9 | Comparative Example 10 | Comparative Example 11 | Comparative Example 12 | Comparative Example 13 | Comparative Example 14 |
|---|---|---|---|---|---|---|---|---|
| Drug substance | Maleate of compound A | 1 | 1 | 1 | 1 | 1 | 1 | 1 |
| Additive | L-arginine | 1 | | | | | | |
|  | L-lysine | | 1 | | | | | |
|  | Malonic acid | | | 1 | | | | |
|  | Tartaric acid | | | | 1 | | | |
|  | Citric acid | | | | | 1 | | |
|  | Lactic acid | | | | | | 1 | |
|  | pH | 8.8 | 9.1 | 2.5 | 2.6 | 2.7 | 2.8 | 4.5 |
|  | Solubility | 18.2 | 10.0 | 140.0 | 139.0 | 59.2 | 87.6 | — |
|  | Bitter taste (post-bitter taste) | 7.4 | 6.6 | 0.0 | 0.0 | 0.0 | 0.5 | 3.0 |
|  | Degradation material (70° C., 7 days) | 0.00% | 0.00% | 1.86% | 3.69% | 3.69% | 0.99% | 0.00% |
|  | Evaluation of bitter taste | C | C | A | A | A | A | C |
|  | Evaluation of degradation material | A | A | C | C | C | C | A |
|  | Comprehensive evaluation | C | C | C | C | C | C | C |

Example 20 (Wet Agitation)

(Formation of Core)

150.0 g of the maleate of compound A, 17.3 g of hydroxypropyl cellulose (HPC-L: product name, Nippon Soda Co., Ltd.), 27.8 g of lactose monohydrate, and 99.0 g of L-aspartic acid were placed in an agitation granulator (vertical granulator model FM-VG-01, manufactured by Powrex Corporation) and sprayed with 60.0 g of 10% by mass of hydroxypropyl cellulose (HPC-L: product name. Nippon Soda Co., Ltd.) aqueous solution while agitated at a blade rotation speed of 270 rpm and a cross screw rotation speed of 2500 rpm. Then, agitation was performed for 9 minutes at a blade rotation speed of 800 rpm and a cross screw rotation speed of 2500 rpm. The whole amount of the obtained granulated material was dried using a fluidized bed granulator (model FD-MP-01, manufactured by Powrex Corporation) at an air supply temperature of 60° C. to obtain a core.

(Formation of Polymer Layer)

Among die obtained cores, a core having a particle size of 100 μm to 355 μm was recovered using a sieve; 10 g of the core was placed in a micro fluidized-bed apparatus (manufactured by Dalton) which was a fluidized bed granulator; the air supply temperature was set to room temperature (30 to 40° C.); a coating solution containing ethylcellulose (Aquacoat ECD: product name, FMC), triacerine, and purified water was fed into the micro fluidized-bed apparatus at a rate of 0.2 to 0.3 g/minute to perform spray coating; and thereby a polymer layer was formed.

(Formation of Overcoat Layer)

After forming the polymer layer, a solution containing mannitol and purified water (the content of mannitol is 14%) was fed into the micro fluidized-bed apparatus at a rate of 0.3 g/minute to obtain particles comprising an overcoat layer on the surface of the polymer layer. Among the obtained particles, particles having a particle size of 100 μm to 425 μm were recovered using a sieve and used for various evaluations.

Example 21 (Wet Agitation)

(Formation of Core)

A core was formed in the same manner as in Example 1.

(Formation of Polymer Layer)

A polymer layer was formed in the same manner as in Example 20 except that the composition of the coating solution was changed to die composition shown in the following table.

Example 22 (Wet Agitation)

(Formation of Core)

The core was obtained in the same manner as in Example 20 except that the amount of lactose monohydrate used was 126.8 g and L-aspartic acid was not used.

(Formation of Polymer Layer)

A polymer layer was formed in the same manner as in Example 20 except that the maleate of compound A comprising methacrylic acid copolymer LD, triethyl citrate, glyceryl monostearate, and polysorbate 80 was used as a coating solution.

(Formation of Overcoat Layer)

An overcoat layer was formed in the same manner as in Example 20.

Comparative Example 15 (Wet Agitation)

(Formation of Core)

The core was obtained in the same manner as in Example 20 except that the amount of lactose monohydrate used was 126.8 g and L-aspartic acid was not used.

(Formation of Polymer Layer)

A polymer layer was formed in the same manner as in Example 20.

(Formation of Overcoat Layer)

An overcoat layer was formed in the same manner as in Example 20.

Example 23 (Wet Agitation)

(Formation of Core)

A core was formed in the same manner as in Example 20.

(Formation of Polymer Layer)

A polymer layer was formed in the same manner as in Example 20.

(Formation of Overcoat Layer)

After forming the overcoat layer in the same manner as in Example 20, a solution containing sodium lauryl sulfate and purified water (the content of sodium lauryl sulfate is 5%) was fed into the micro fluidized-bed apparatus at a rate of 0.3 g/minute to obtain panicles and among the obtained particles, panicles having a panicle size of 100 μm to 425 μm were recovered using a sieve. After further adding L-aspartic acid as powder to the obtained particles, tire particles obtained by mixing for 5 minutes were used for various evaluations.

Example 24 (Wet Agitation)

(Formation of Core)

A core was formed in the same manner as in Example 20.

(Formation of Polymer Layer)

A polymer layer was formed in the same manner as in Example 20.

(Formation of Overcoat Layer)

After forming the overcoat layer in the same manner as in Example 20. L-aspartic acid was added as powder and then the particles obtained by mixing for 5 minutes were used for various evaluations.

[Evaluation]

The following items were evaluated for the pharmaceutical compositions manufactured in Examples 20 to 24 and Comparative Example 15. The results of the evaluation are shown in Table 7.

<pH>

The pH was measured when the solid pharmaceutical composition was dissolved or suspended in a 10 mmol/L KCl solution such that the concentration of the malate of compound A reached to 8.96 mg/mL.

<Evaluation of Bitter Taste (Post-Bitter Taste)>

Evaluation was performed in the same manner as described in Examples 1 to 19 and Comparative Examples 1 to 14.

However, the measurement method is as follows. The pharmaceutical composition was added to Japanese Pharmacopoeia purified water such that the concentration of the maleate of compound A was 9 mg/mL, and mixed by invasion for 30 seconds. The solution was immediately filtered through a polysilicate glass fiber, and the solution to which KCl was added such that the KCl concentration in the filtrate was 10 mmol/L was used as a sample solution. In addition, a 10 mmol/L KCl solution was used as a control solution.

The criteria for evaluation are as follows.

A: Less than 0.6
B: 0.6 or more and less than 1.0
C: 1.0 or more

<Evaluation of Degradation Material>

Evaluation was performed in the same manner as described in Examples 1-19 and Comparative Examples 1-14.

<Comprehensive Evaluation>

The comprehensive evaluation criteria are the same as the comprehensive evaluation in Examples 1 to 19 and Comparative Examples 1 to 14.

TABLE 7

A numerical value of each component in the table shows parts by mass

|  |  | Example 20 | Example 21 | Example 22 | Example 23 | Example 24 | Comparative Example 15 |
|---|---|---|---|---|---|---|---|
| Core | Maleate of compound A | 448 | 448 | 448 | 448 | 448 | 448 |
|  | Hydroxypropyl cellulose | 69 | 69 | 69 | 25 | 69 | 69 |
|  | Lactose monohydrate | 83 | 83 | 379 |  | 334 | 379 |
|  | Carmellose Ca |  |  |  |  | 45 |  |
|  | L-aspartic acid | 296 | 296 |  |  |  |  |
| Polymer layer | Etyl cellulose | 326 | 100 |  | 95 | 326 | 326 |
|  | Ethyl acrylate/methyl methacrylate copolymer |  |  |  | 28 |  |  |
|  | Triacetin | 82 | 25 |  | 14 | 82 | 82 |
|  | Methacrylic acid copolymer LD |  |  | 349 |  |  |  |
|  | Triethyl citrate |  |  | 35 |  |  |  |
|  | Glyceryl monostearate |  |  | 17 |  |  |  |
|  | Polysorbate 80 |  |  | 7 |  |  |  |
| Overcoat layer | Mannitol | 80 |  | 94 | 78 | 94 | 80 |
|  | Light anhydrous silicic acid |  | 10 |  |  |  |  |

TABLE 7-continued

A numerical value of each component in the table shows parts by mass

|  | Example 20 | Example 21 | Example 22 | Example 23 | Example 24 | Comparative Example 15 |
|---|---|---|---|---|---|---|
| Lauryl sulfate Na |  |  |  | 58 |  |  |
| L-aspartic acid |  |  |  | 22 | 90 |  |
| pH | 3.8 | 3.9 | 4.2 | 3.5 | 3.2 | 4.9 |
| Bitter taste (post-bitter taste) | A | A | A | A | A | C |
| Degradation material (70° C., 7 days) | A | A | B | A | A | A |
| Comprehensive evaluation | A | A | B | A | A | C |

Example 25

(Formation of Core)

A core was obtained in the same manner as in Example 23 except that L-aspartic acid was not used.

(Formation of Polymer Layer)

A polymer layer was formed in the same manner as in Example 23.

(Formation of Overcoat Layer)

An overcoat layer was formed in the same manner as in Example 24.

The fine granules obtained above and the excipient component were mixed in such a way as to provide the composition shown in Table 8, to obtain a tableted powder (mixed powder). The tableted powder (mixed powder) obtained was weighed out such that 448 mg of tire maleate of compound A was contained in 3 tablets and was compression molded using a rotary tableting machine (product name: HT-AP-SS, Hata Tekkosho Co., Ltd.) with a 12 mmφ single R. face punch at a rotational speed of 20 rpm in such a way as to provide a hardness of 50 N, to obtain an orally disintegrating tablet (tablet).

TABLE 8

|  |  |  |  | Example 25 |
|---|---|---|---|---|
| Fine granule | Core | Maleate of compound A | 448 | 49.3 |
|  |  | Hydroxypropyl cellulose | 25 |  |
|  | Polymer layer | Ethyl cellulose | 149 |  |
|  |  | Ethyl acrylate/methyl methacrylate copolymer | 45 |  |
|  |  | Triacetin | 22 |  |
|  | Overcoat layer | Mannitol | 84 |  |
| Granulated material of mannitol/corn starch |  |  |  | 17.8 |
| Crospovidone |  |  |  | 3.0 |
| Ethyl cellulose |  |  |  | 3.9 |
| Mg aluminometasilicate |  |  |  | 2.5 |
| Crystalline cellulose |  |  |  | 19.7 |
| Hydrous silicon dioxide |  |  |  | 1.0 |
| Aspartame |  |  |  | 1.0 |
| Strawberry micron |  |  |  | 0.1 |
| Ca stearate |  |  |  | 0.3 |
| L-aspartic acid |  |  |  | 1.4 |

[Evaluation of Orally Disintegrating Tablet]
<Evaluation of Bitter Taste Masking>

One orally disintegrating tablet was placed in the oral cavity of the subject. Evaluation was performed according to the following evaluation criteria whether bitter taste derived from compound A remained 60 minutes after the placement.
Evaluation Criteria:
B A bitter taste was slightly felt 60 minutes after the placement
A No bitter taste was felt 60 minutes after the placement
The orally disintegrating tablet obtained in Example 25 was subjected to sensory evaluation of bitter taste masking.

As a result, for the orally disintegrating tablet in Example 25, no bitter taste was felt, and the bitter taste derived from compound A was sufficiently masked.
<Oral Disintegration Time>

One orally disintegrating tablet was dosed in the oral cavity of one adult male, and the time until the core of the tablet was not felt was measured.

The oral disintegration time of the orally disintegrating tablet in Example 25 was measured. As a result, the oral disintegration time was 25 seconds.
<pH of Orally Disintegrating Tablet>

The orally disintegrating tablet was added to Japanese Pharmacopoeia purified water such that the concentration of the maleate of compound A was 9 mg/mL, and mixed by inversion for 30 seconds. The solution was immediately filtered through a polysilicate glass fiber, and tire solution to which KCl was added such that the KCl concentration in the filtrate was 10 mmol/L was used as a sample solution. In addition, a 10 mmol/L KCl solution was used as a control solution.

The pH of the orally disintegrating tablet in Example 25 was measured. As a result, the pH was 3.7.

REFERENCE SIGNS LIST

5 Core
6 Polymer layer
7 Overcoat layer

The invention claimed is:

1. A solid pharmaceutical composition comprising 1-(3-(2-(1-benzothiophen-5-yl)ethoxy)propyl)azetidin-3-ol or a salt thereof and a carboxylic acid whose solubility in water at 25° C. is 50 g/100 g H$_2$O or less, wherein the carboxylic acid is one or more selected from the group consisting of maleic acid, L-glutamic acid hydrochloride, fumaric acid, ascorbic acid, L-aspartic acid, succinic acid, adipic acid, sorbic acid, L-glutamic acid, carboxy vinyl polymer, hypromellose phthalate, cellulose acetate phthalate, carboxymethyl ethyl cellulose, and L-arginine hydrochloride, and the pH of a solution obtained when the solid pharmaceutical composition is dissolved or suspended in a 10 mmol/L KCl solution such that 1-(3-(2-(1-benzothiophen-5-yl)ethoxy)propyl)azetidin-3-ol or the salt thereof is 1 mg/mL or 8.96 mg/mL is 4.8 or less.

2. The solid pharmaceutical composition according to claim 1, wherein the carboxylic acid is one or more selected from L-aspartic acid or L-glutamic acid.

3. The solid pharmaceutical composition according to claim 1, wherein the pH is 3.0 or more and 4.8 or less.

4. The solid pharmaceutical composition according to claim 1, wherein the solid pharmaceutical composition is a composition comprising fine granules comprising 1-(3-(2-(1-benzothiophen-5-yl)ethoxy)propyl)azetidin-3-ol or the salt thereof and the carboxylic acid whose solubility in water at 25° C. is 50 g/100 g $H_2O$ or less.

5. The solid pharmaceutical composition according to claim 4, wherein the fine granules are fine granules having a core comprising at least 1-(3-(2-(1-benzothiophen-5-yl)ethoxy)propyl)azetidin-3-ol or the salt thereof and a binder, and a polymer layer with which a surface of the core is coated.

6. The solid pharmaceutical composition according to claim 4, wherein the content of the carboxylic acid in fine granules is 10 to 100% by mass based on the mass of 1-(3-(2-(1-benzothiophen-5-yl)ethoxy)propyl)azetidin-3-ol or the salt thereof.

7. The solid pharmaceutical composition according to claim 1, wherein the composition is a fine granule or a tablet.

8. The solid pharmaceutical composition according to claim 1, wherein the composition is an orally disintegrating tablet.

9. A solid pharmaceutical composition comprising 1-(3-(2-(1-benzothiophen-5-yl)ethoxy)propyl)azetidin-3-ol or a salt thereof and a carboxylic acid whose solubility in water at 25° C. is 50 g/100 g $H_2O$ or less, wherein the pH of a solution obtained when the solid pharmaceutical composition is dissolved or suspended in a 10 mmol/L KCl solution such that 1-(3-(2-(1-benzothiophen-5-yl)ethoxy)propyl)azetidin-3-ol or the salt thereof is 1 mg/mL or 8.96 mg/mL is 4.8 or less, the solid pharmaceutical composition is a composition comprising fine granules comprising 1-(3-(2-(1-benzothiophen-5-yl)ethoxy)propyl)azetidin-3-ol or the salt thereof and the carboxylic acid whose solubility in water at 25° C. is 50 g/100 g $H_2O$ or less, and the fine granules are fine granules having a core comprising at least 1-(3-(2-(1-benzothiophen-5-yl)ethoxy)propyl)azetidin-3-ol or the salt thereof and a binder, and a polymer layer with which a surface of the core is coated.

* * * * *